(12) United States Patent
Michels et al.

(10) Patent No.: US 7,691,615 B2
(45) Date of Patent: *Apr. 6, 2010

(54) PROCESS FOR THE PRODUCTION OF PIPERIDINE DERIVATIVES WITH MICROORGANISMS

(75) Inventors: Peter C. Michels, Des Moines, IA (US); Eric L. Zirbes, Coralville, IA (US)

(73) Assignee: Albany Molecular Research, Inc., Albany, NY (US)

( * ) Notice: Subject to any disclaimer, the term of this patent is extended or adjusted under 35 U.S.C. 154(b) by 161 days.
This patent is subject to a terminal disclaimer.

(21) Appl. No.: 11/624,096
(22) Filed: Jan. 17, 2007
(65) Prior Publication Data
US 2007/0134774 A1  Jun. 14, 2007

Related U.S. Application Data

(63) Continuation of application No. 10/638,841, filed on Aug. 11, 2003, now Pat. No. 7,232,908, which is a continuation of application No. 09/754,786, filed on Jan. 4, 2001, now Pat. No. 6,613,907, which is a continuation-in-part of application No. 09/708,959, filed on Nov. 8, 2000, now abandoned.

(51) Int. Cl.
*C12P 17/21* (2006.01)
(52) U.S. Cl. ............... 435/122; 514/317; 546/239; 546/240; 546/241
(58) Field of Classification Search ........... 546/239, 546/340, 241; 435/122, 135, 136; 514/317
See application file for complete search history.

(56) References Cited

U.S. PATENT DOCUMENTS

| 3,419,469 | A | 12/1968 | Humphrey et al. |
| 3,649,453 | A | 3/1972 | Herr et al. |
| 3,966,553 | A | 6/1976 | Charpentier et al. |
| 4,564,594 | A | 1/1986 | Goldberg et al. |
| 5,032,513 | A | 7/1991 | Page et al. |
| 5,135,859 | A | 8/1992 | Witholt et al. |
| 5,204,249 | A | 4/1993 | Schwartz et al. |
| 5,990,127 | A | 11/1999 | Meiwes et al. |
| 6,613,907 | B2 | 9/2003 | Michels et al. |
| 7,232,908 | B2 | 6/2007 | Michels et al. |

FOREIGN PATENT DOCUMENTS

WO   WO 99/47693   9/1999

OTHER PUBLICATIONS

Schwartz et al. "Microbial Oxidation of Ebastine", Applied Microbiology and Biotechnology, vol. 44, No. 6, 1996, pp. 731-735, XP-002305265.
Umezawa et al., "Microbial production of orabole," CA 84:178218 (1976).
Search Report for European Patent Application No. 08005953.8.

*Primary Examiner*—Celia Chang
(74) *Attorney, Agent, or Firm*—Heslin Rothenberg Farley & Mesiti P.C.

(57) ABSTRACT

The present invention relates to the production of a product compound having a structure according to Formulae IA and/or IB:

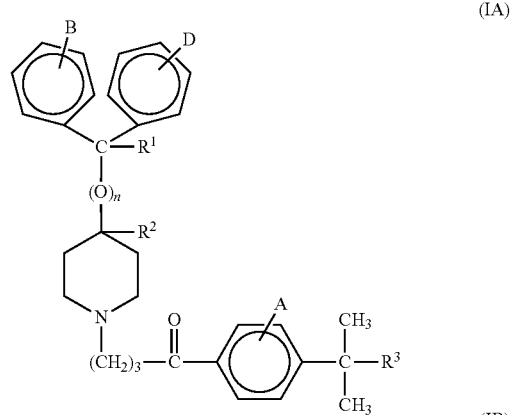

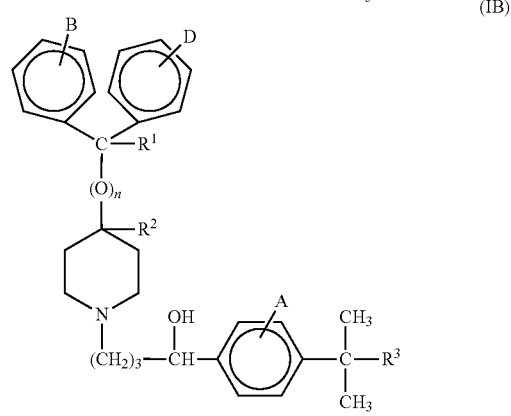

wherein
n is 0 or 1;
$R^1$ is hydrogen or hydroxy;
$R^2$ is hydrogen;
or, when n is 0, $R^1$ and $R^2$ taken together form a second bond between the carbon atoms bearing $R^1$ and $R^2$, provided that when n is 1, $R^1$ and $R^2$ are each hydrogen;
$R^3$ is —COOH or —COOR$^4$;
$R^4$ is an alkyl or aryl moiety;
A, B, and D are the substituents of their rings, each of which may be different or the same, and are selected from the group consisting of hydrogen, halogens, alkyl, hydroxy, and alkoxy.

This process involves incubating a starting compound having a structure according to Formulae IIA and/or IIB:

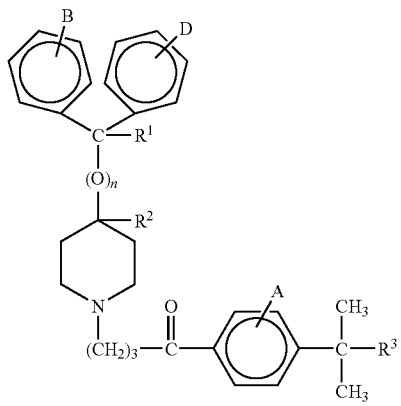

-continued

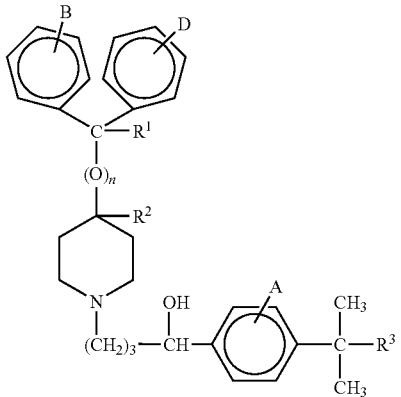

(IIB)

wherein $R^3$ is —$CH_3$ and $R^1$, $R^2$, A, B, and D are defined above in the presence of a microorganism under conditions effective to produce the product compound. The microorganism can be from the genus *Streptomyces, Stemphylium, Gliocladium, Bacillus, Botrytis, Cyathus, Rhizopus, Pycniodosphora, Pseudomonas, Helicostylum, Aspergillus, Mucor, Gelasinospora, Rhodotorula, Candida, Mycobacterium,* or *Penicilluc*. Alternatively, the microorganism can be *Cunninghamella baineri*.

3 Claims, No Drawings

PROCESS FOR THE PRODUCTION OF PIPERIDINE DERIVATIVES WITH MICROORGANISMS

CROSS REFERENCE TO RELATED APPLICATIONS

This application is a continuation of pending U.S. patent application Ser. No. 10/638,841, filed Aug. 11, 2003, which is a continuation of U.S. patent application Ser. No. 09/754,786, filed Jan. 4, 2001, now U.S. Pat. 6,613,907, which is a continuation-in-part of U.S. patent application Ser. No. 09/708,959, filed Nov. 8, 2000, now abandoned. All are incorporated herein by reference in their entirety.

FIELD OF THE INVENTION

The present invention relates to a process for the production of piperidine derivatives with microorganisms.

BACKGROUND OF THE INVENTION

Terfenadine, 1-(p-tert-butylphenyl)-4-[4'-(α-hydroxy-diphenylmethyl)-1'-piperidinyl]-butanol is a non-sedating anti-histamine. It is reported to be a specific $H^1$-receptor antagonist that is also devoid of any anticholingeric, anti-serotoninergic, and anti-adrenergic effects both in vitro and in vivo. See D. McTavish, K. L. Goa, M. Ferrill, *Drugs,* 1990, 39, 552; C. R. Kingsolving, N. L. Monroe, A. A. Carr, *Pharmacologist,* 1973, 15, 221; J. K. Woodward, N. L. Munro, *Arzneim-Forsch,* 1982, 32, 1154; K. V. Mann, K. J. Tietze, *Clin. Pharm.* 1989, 6, 331. A great deal of effort has been made investigating structure-activity relationships of terfenadine analogs, and this is reflected in the large number of U.S. patents disclosing this compound and related structures as follows:

U.S. Pat. No. 3,687,956 to Zivkovic
U.S. Pat. No. 3,806,526 to Carr, et. al.
U.S. Pat. No. 3,829,433 to Carr, et. al.
U.S. Pat. No. 3,862,173 to Carr, et. al.
U.S. Pat. No. 3,878,217 to Carr, et. al.
U.S. Pat. No. 3,922,276 to Duncan, et. al.
U.S. Pat. No. 3,931,197 to Carr, et. al.
U.S. Pat. No. 3,941,795 to Carr, et. al.
U.S. Pat. No. 3,946,022 to Carr, et. al.
U.S. Pat. No. 3,956,296 to Duncan, et. al.
U.S. Pat. No. 3,965,257 to Carr, et. al.
U.S. Pat. No. 4,742,175 to Fawcett, et. al.

In animal and human metabolic studies, terfenadine has been shown to undergo extensive hepatic first-pass metabolism, and, after usual dosages it cannot be detected in plasma unless very sensitive assays are used. A specific hepatic cytochrome P-450 enzyme converts terfenadine to the major metabolite 4-[4-[4-(hydroxydiphenylmethyl)-1-piperidinyl]-1-hydroxybutyl]-α,α-dimethylphenylacetic acid, also known as terfenadine carboxylic acid metabolite. This metabolite can be readily detected in plasma and is considered to be the active form of orally administered terfenadine.

Side effects reported with terfenadine are cardiac arrhythmias (ventricular tachyarrhythmias, torsades de points, ventricular fibrillation), sedation, GI distress, dry mouth, constipation and/or diarrhea. The most serious of these, and potentially life threatening, are cardiac arrhythmias, which are related to terfenadine's ability to prolong the cardiac QT interval, and are only reported in patients administered terfenadine with liver disease or who also take the antifungal drug ketoconazole or the antibiotic erythromycin.

Since cardiac side effects of terfenadine have been reported in patients with impaired liver function, as well as in patients also taking antibiotics known to suppress hepatic enzyme function, it was speculated that the cardiac side effects were due to accumulation of terfenadine and not due to accumulation of terfenadine carboxylic acid metabolite. Patch clamp studies in isolated feline ventricular myocytes support the contention that terfenadine, and not the carboxylic acid metabolite, is responsible for cardiac side effects. At a concentration of 1 μM, terfenadine caused a greater than 90% inhibition of the delayed rectifier potassium current. At concentrations up to 5 μM, the terfenadine carboxylic acid metabolite had no significant effect on the potassium current in this assay (See R. L. Woosley, Y. Chen, J. P. Frieman, and R. A. Gillis, *JAMA* 1993, 269, 1532). Since inhibition of ion transport has been linked to cardiac abnormalities, such as, arrhythmias, these results indicate that terfenadine carboxylic acid is likely not liable to cause cardiac arrhythmias, at dose levels at which there is a distinct risk of such a side effect being caused by terfenadine itself.

Carebastine, 4-[4-[4-(diphenylmethoxy)-1-piperidinyl]-1-oxobutyl]-α,α-dimethylphenylacetic acid, is the carboxylic acid metabolite of ebastine, 1-(p-tert-butylphenyl)-4-[4'-(α-diphenylmethoxy)-1'-piperidinyl]-butanol. Both compounds possess potent selective histamine $H_1$-receptor blocking and calcium antagonist properties and should prove useful in the treatment of a variety of respiratory, allergic, and cardiovascular disease states.

These compounds relax bronchial and vascular smooth muscle in vitro and in vivo and inhibit the constrictor influence of noradrenaline, potassium ions, and various other agonist drugs. The compounds also inhibit responses of intestinal and tracheal preparations to histamine, acetylcholine, and barium chloride and block the bronchoconstriction induced by histamine aerosol in guinea pigs in doses less than 1 mg/kg animal body weight administered orally. They also possess antianaphylactin properties in the rat, inhibit the skin lesions to a variety of anaphylactic mediators (histamine, 5-hydroxytryptamine, bradykinin, $LCD_4$, etc.), and antagonize the Schultz-Dale response in the sensitive guinea-pig.

Piperidine derivatives related to the terfenadine carboxylic acid metabolite are disclosed in the following U.S. patents:

U.S. Pat. No. 4,254,129 to Carr, et. al.
U.S. Pat. No. 4,254,130 to Carr, et. al.
U.S. Pat. No. 4,285,957 to Carr, et. al.
U.S. Pat. No. 4,285,958 to Carr, et. al.

In these patents, 4-[4-[4-(hydroxydiphenylmethyl)-1-piperidinyl]-1-hydroxybutyl]-α,α-dimethylbenzeneacetic acid and related compounds are prepared by alkylation of a substituted piperidine derivative of the formula:

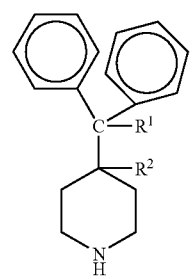

with an α-haloalkyl substituted phenyl ketone of the formula:

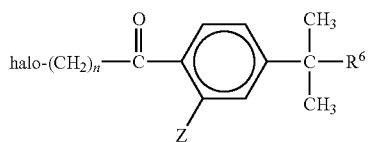

wherein the substituents halo, $R^1$, $R^2$, n, Z, and $R^6$ are described in column 6 of U.S. Pat. No. 4,254,130.

In similar fashion, U.S. Pat. No. 4,550,116 to Soto et al. describes preparation of piperidine derivatives related to carebastine by reacting the α-haloalkyl substituted phenyl ketone with a substituted hydroxypiperidine derivative of the formula:

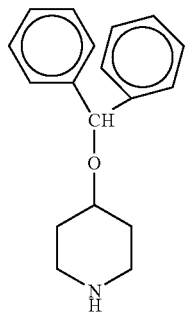

U.S. Pat. No. 4,254,130 indicates that α-haloalkyl substituted phenyl ketones, wherein Z is hydrogen, are prepared by reacting an appropriate straight or branched lower alkyl $C_{1-6}$ ester of α,α-dimethylphenylacetic acid with a compound of the following formula:

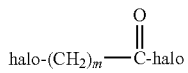

under the general conditions of a Friedel-Crafts acylation, wherein halo and m are described in column 11 of U.S. Pat. No. 4,254,129. The reaction is carried out in carbon disulfide as the preferred solvent.

Other procedures for synthetically producing terfenadine carboxylic acid metabolite are disclosed in U.S. Pat. Nos. 5,578,610, 5,581,011, 5,589,487, 5,663,412, 5,750,703 and 5,994,549, as well as PCT Application Nos. WO95/00492, WO94/03170, and WO95/00480.

Another approach to producing terfenadine carboxylic acid metabolite-like compounds involves the conversion of terfenadine-like compounds using fungi. This procedure is disclosed in U.S. Pat. No. 5,204,249 to Schwartz et. al. and U.S. Pat. No. 5,990,127 to Meiwes et. al. In the Schwartz patent, fungi from the genus *Cunninghamella* are used to convert ebastine to carebastine. The Meiwes patent employs fungi species from the genera *Cunninghamella* and *Absidia* to transform terfenadine to its acid metabolite. Although these procedures have been found to be useful in producing terfenadine carboxylic acid metabolite-like compounds, the initial yield of these products from such process is quite low and the restriction to filamentous fungi, from these genera previously identified, creates undesirable limitations for a commercially viable process.

The present invention is directed toward an improved process for preparation of terfenadine carboxylic acid metabolite and carebastine derivatives using microbial catalysts.

SUMMARY OF THE INVENTION

The present invention relates to the production of a product compound having the Formulae IA and/or IB:

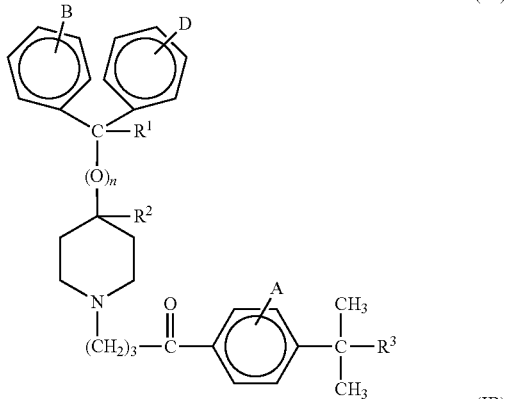

(IA)

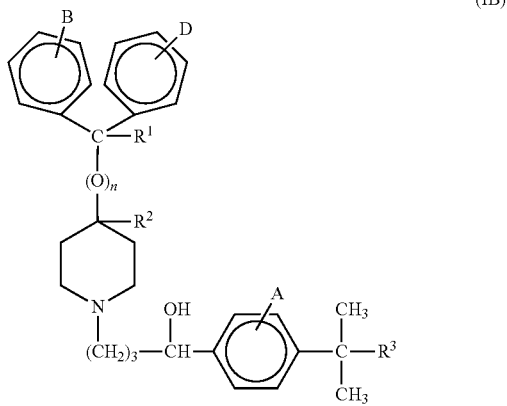

(IB)

wherein
n is 0 or 1;
$R^1$ is hydrogen or hydroxy;
$R^2$ is hydrogen;
or, when n is 0, $R^1$ and $R^2$ taken together form a second bond between the carbon atoms bearing $R^1$ and $R^2$, provided that when n is 1, $R^1$ and $R^2$ are each hydrogen;
$R^3$ is —COOH or —COOR$^4$;
$R^4$ is an alkyl or aryl moiety;
A, B, and D are the substituents of their rings, each of which may be different or the same, and are selected from the group consisting of hydrogen, halogens, alkyl, hydroxy, and alkoxy.

This process involves incubating a starting compound having the Formulae IIA and/or IIB:

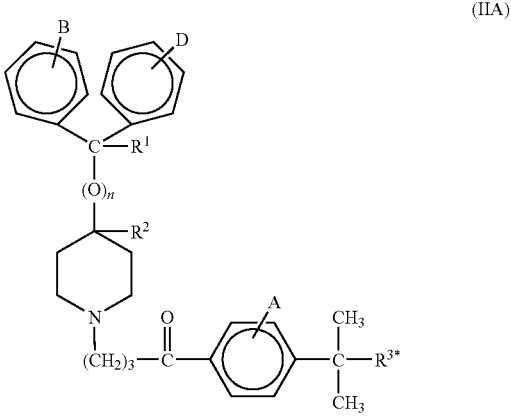

(IIA)

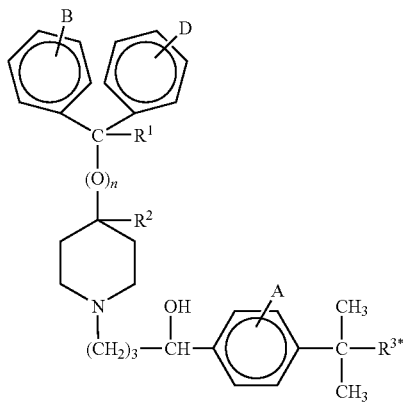

(IIB)

wherein R³* is —CH₃ and R¹, R², A, B, and D are defined above in the presence of a microorganism under conditions effective to produce the product compound. The microorganism can be from the genus *Streptomyces, Stemphylium, Gliocladium, Bacillus, Botrytis, Cyathus, Rhizopus, Pycniodosphora, Pseudomonas, Helicostylum, Aspergillus, Mucor, Gelasinospora, Rhodotorula, Candida, Mycobacterium*, or *Penicillium*.

The present invention also relates to the production of a product compound having a structure according to Formulae IA and/or IB by incubating a starting compound having a structure according for Formulae IIA and/or IIB in the presence of *Cunninghamella bainieri* under conditions effective to produce the product compound.

The present invention provides an alternative and/or improved process for the preparation of carboxyterfenadine from terfenadine. The selectivity and yields of carboxyterfenadine obtained using the strains and processes according to the present invention can be higher than those obtained using known strains. In addition, the identification of many strains, especially bacterial strains (both gram positive and gram negative), for the target conversion, can permit significant strain improvement, processing, and manufacturing advantages over previously used filamentous fungal strains.

Importantly, and surprisingly, *Streptomyces, Bacillus*, and *Pseudomonas* represent gram positive and gram negative eubacterial strains, an entirely different kingdom from the filamentous fungi previously identified to perform the target transformation. Techniques for strain improvement and genetic manipulation of bacterial strains, including especially *Streptomyces, Bacillus*, and *Pseudomonas* species, are considerably simpler and better established compared with fungi, such as *Cunninghamella* strains. Moreover, commercial-scale processing of non-filamentous microorganisms, including non-filamentous fungi, yeasts, and eubacteria, provides many additional and more economical fermenter and purification processes than are feasible for filamentous fungi alone.

Moreover, the variety of microbial biocatalysts allow for the transformation to a broad variety of structural variations. In addition, the identification of multiple strains possessing genes and enzymes useful for such transformation is an important prerequisite to the use of modern molecular biological techniques for the further optimization of microorganisms as industrial catalysts for the production of piperidine derivatives.

DETAILED DESCRIPTION OF THE INVENTION

The present invention relates to the production of a product compound having a structure according to Formulae IA and/or IB:

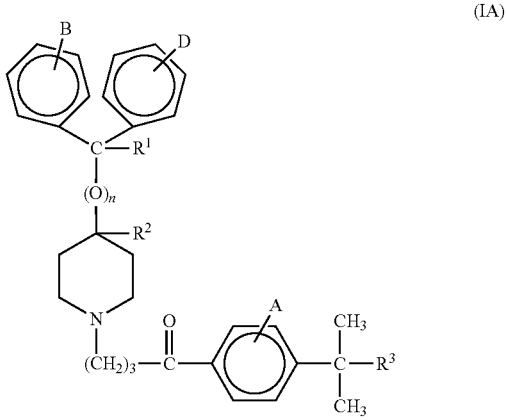

(IA)

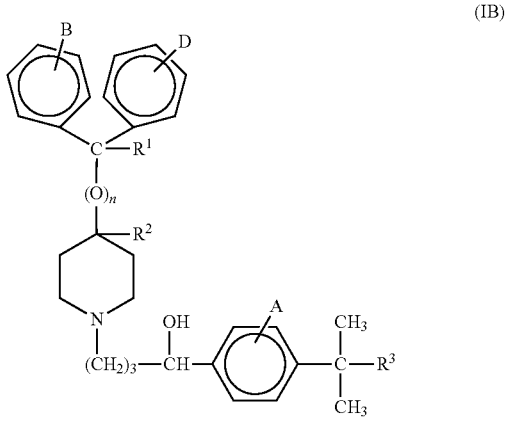

(IB)

wherein
n is 0 or 1;
R¹ is hydrogen or hydroxy;
R² is hydrogen;
or, when n is 0, R¹ and R² taken together form a second bond between the carbon atoms bearing R¹ and R², provided that when n is 1, R¹ and R² are each hydrogen;
R³ is —COOH or —COOR⁴;
R⁴ is an alkyl or aryl moiety;
A, B, and D are the substituents of their rings, each of which may be different or the same, and are selected from the group consisting of hydrogen, halogens, alkyl, hydroxy, and alkoxy.

This process involves incubating a starting compound having a structure according to Formulae IIA and/or IIB:

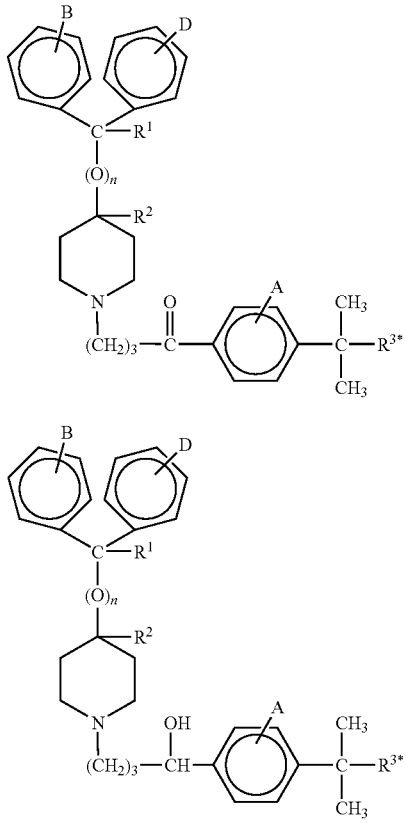

wherein $R^{3*}$ is —$CH_3$ and $R^1$, $R^2$, A, B, and D are defined above, in the presence of a microorganism under conditions effective to produce the product compound. The microorganism can be from the genus *Streptomyces, Stemphylium, Gliocladium, Bacillus, Botrytis, Cyathus, Rhizopus, Pycniodosphora, Pseudomonas, Helicostylum, Aspergillus, Mucor, Gelasinospora, Rhodotorula, Candida, Mycobacterium,* or *Penicillium.*

The present invention also relates to the production of a product compound having a structure according to Formulae IA and/or IB by incubating a starting compound having a structure according to Formulae IIA and/or IIB in the presence of *Cunninghamella bainieri* under conditions effective to produce the product compound.

The process of the present invention is carried out in a liquid growth medium. What constitutes an appropriate growth medium is dependent on the specific microorganism and purpose, as is familiar to those trained in the art. In general, the growth medium contains carbon sources, such as dextrose, sucrose, citrate, and/or starch, and nitrogen sources, such as soybean flour, yeast extract, tryptone, malt extract, and/or ammonium acetate. In addition, the growth media contains inorganic salts, such as sodium phosphate, potassium phosphate, sodium chloride, calcium chloride, calcium sulfate, calcium carbonate, and/or magnesium sulfate, and trace elements, such as iron, zinc, copper, molybdenum, manganese, or other metal salts.

The microorganisms used in the present invention can be selected from the following genera: *Streptomyces, Stemphylium, Gliocladium, Bacillus, Botrytis, Cyathus, Rhizopus, Pycniodosphora, Pseudomonas, Helicostylum, Aspergillus, Mucor, Gelasinospora, Rhodotorula, Candida, Mycobacterium,* or *Penicillium.* For the genus *Streptomyces,* suitable species include *Streptomyces catenulae, Streptomyces cavourensis, Streptomyces rimosus,* and *Streptomyces griseus.* For the genus *Stemphylium, Stemphylium consortiale* is a suitable species. Useful *Aspergillus* species include *Aspergillus aliaceus, Aspergillus carbonarium (Bainier) Thom, Aspergillus flavipes, Aspergillus fumigatus, Aspergillus ochraceous,* and *Aspergillus terricola.* As to the genus *Gliocladium,* the species *Gliocladium deliquescens* is particularly useful. With regard to the *Bacillus* genus, the species *Bacillus cereus, Bacillus subtilis,* and *Bacillus fusiformis* can be used to carry out the process of the present invention. A suitable species of *Botrytis* is *Botrytis allii.* As to the genus *Cyathus,* the species *Cyathus striatus* can be used. *Rhizopus oryzae* is a representative member of the *Rhizopus* genus which can be used to carry out the present invention. Useful *Pseudomonas* species include *Pseudomonas putida.* With regard to the *Pycniodosphora* genus, the species *Pycniodosphora dispersa* can be used. For the *Helicostylum* genus, the species *Helicostylum piriforme* can be used to carry out the process of the present invention. As to the *Mucor* genus, the species *Mucor circinelloides f. griseo-cyanus, Mucor recurvatus,* and *Mucor mucedo* can be used to carry out the present invention. The species *Gelasionospora autosteria* is a member of the *Gelasionospora* genus which is suitable for carrying out the process of the present invention. With respect to the genus *Rhodotorula,* the species *Rhodotorula rubra* can be used. For the genus *Penicillium,* the species *Penicillium notatum* and *Penicillium chyrsogenum* can be used to practice the process of the present invention. With regard to the *Candida* genus, the species *Candida guilliermondii, Candida lipolytica,* and *Candida parasilosis* var. *quercus* can be utilized. Suitable *Mycobacterium* species include *Mycobacterium bisrymcum.*

For each strain, the invention relates to the use of the whole microorganism, and components thereof, including, but not limited to, cell extracts, microsomes, isolated enzymes, and genes, for the chemo- and regioselective oxidation of Formulae IIA and/or IIB to products of Formulae IA and/or IB Furthermore, mutants and selectants of the microbes of the listed genera and especially those of the specific strains described herein, are also suitable for use in the process of the present invention. Mutants can be created by classical methods of mutagenesis for strain improvement, such as random mutagenesis mediated by chemicals or electromagnetic waves, or by modern methods for genetic manipulation, such as error prone PCR, codon mutagenesis, or gene shuffling.

Another aspect of the present invention relates to the use of the species *Cunninghamella bainieri* in carrying out the process of the present invention.

The present invention also relates to the discovery and use of microorganisms of the genera *Streptomyces, Gliocladium,* and *Stemphyllium* to perform as superior agents for the selective oxidation of terfenadine (Formulae IIA/IIB) to carboxyterfenadine (Formulae IA/IB) compared with fungi of the genera *Cunninghamella* and *Absidia.* (IIB)

Additionally, microbial strains of the genera *Botrytis, Rhizopus, Cyathus, Bacillus, Pycniodosphora, Pseudomonas, Helicostylum, Aspergillus, Gelasinospora, Rhodotorula, Penicillium,* and *Candida* have also been identified as oxidizing terfenadine to carboxyterfenadine in yields greater than 3% without optimization. In prior experimentation, Meiwes et al. identified only two strains that produced yields of 3% or greater during initial screening.

Moreover, microorganisms from the genera *Ascoidia, Enterococcus, Fusidium, Lentinus, Lophotrichus, Mycobacterium, Polyporus, Spicaria,* and *Trichophyton* have been found to be biocatalysts capable of oxidizing terfenadine to carboxyterfenadine.

All of these microorganisms are freely available from public culture collections. The specific identity and source of microbial cultures are described in the examples below.

Microbial cultures used for the present invention can be maintained according to procedures well known to those skilled in the art, such as on solid media, preserved in mineral oil and lyophilized or frozen.

Microbial cultures can be maintained on an appropriate solid media, such as 30 grams/liter of sabouraud dextrose broth and 20 grams/liter of agar. Preferably, for some strains, preparation of inocula including a low temperature cryopreservation and thawing technique (i.e. the "Cryoready" technique) serves to improve the approach for transforming the starting material to the piperidine product of the present invention by reducing the time required for producing suitable inocula and raising production of the piperidine product. After growing the culture in an appropriate liquid medium, the microbial suspension is centrifuged, the spent liquid medium is removed, and the concentrated cell pellet is resuspended with an equal volume of sterile 20% glycerol stock and fresh broth, to produce a cell suspension in 10% glycerol.

From solid media, the microorganisms are initially propagated through one or more stages in a neutral liquid culture medium appropriate to support the growth of specific strains (i.e. the "Multistage" procedure). Typical media for initial propagation consists of 20 g/l of glucose, 5 g/l of yeast extract, 5 g/l of soybean flour, 5 g/l of NaCl, and 5 g/l of $K_2HPO_4$. The initial stage of microbial cultures was incubated at 29° C. and 250 rpm for 48 or 72 hrs. Subsequent stages were inoculated, with a heavy inoculum (1-20% v/v, especially 10% v/v of the microbial suspension from the previous stage of liquid culture, into fresh liquid medium.

For the reaction stage, a heavy inoculum (1-20% v/v, especially 10% v/v) of the microbial suspension, or of thawed cryopreserved cells are inoculated into fresh medium. The microorganisms are cultured at temperatures between about 20° and 80° C., preferably 25° to 37° C., and at pH from 4 to 9, especially between pH 5 and 8, depending on the specific microorganism used for the transformation. Incubating of the microorganisms was carried out over a time interval of 2-240 hours, preferably from 75 to 170 hours. The reaction was conducted aerobically, initially in parallel, multiwell reaction chambers, continuously supplied with air or enriched oxygen, and agitated. Subsequently, larger scale fermentations can be conducted in a similar manner in shaker flasks, and then in fermenters with stirring and aeration.

The addition of the starting material to the microbial culture is made between 0-72 hours of the inoculation of the reaction medium with prepared inocula, preferably after approximately 8-48 hours and especially after 24 hours of incubation. The addition of the starting material is most expediently carried out from a solution of an appropriate organic solvent, but can also be added as a solid powder, or as a suspension. From solution, the starting material is added most preferably in dimethylformamide (DMF), but also in ethanol, dimethyl sulfoxide (DMSO), dimethylacetamide (DMA), acetonitrile, tetrahydrofuran (THF) and, a formamide (i.e. dibutyl-, diisopropyl-, or diethyl-), a pyrrolidone (i.e. 1-methyl-, 1-ethyl-, 1-cyclohexyl-), 4-formyl-morpholine, 1-formylpiperidine, 1-formylpyrrolidine, tetramethyl-tetraethyl-, tetrabutylurea, a phosphine oxide (i.e. tripiperidino- or tripyrrolidino-), sulfolane, N-methyl-caprolactam, or mixtures thereof. Biocompatible organic solubilizers, such as cyclodextrins or surfactants (e.g., Tween 80 or Pluronic F38) can also be added to the reaction medium containing the microorganism.

The compounds of Formulae IA and/or IB can be isolated directly from the microbial broth or from clarified liquid after separation of the cells, for example, by centrifugation or filtration. These products can be isolated by extraction with organic solvents or by adsorption on hydrophobic resins or ion exchangers.

Additional variations of this invention may use the embodied microorganisms and standard techniques and conventional procedures for incubating the microorganisms and conducting the reactions, as disclosed in generally-available manuals. For instance, methods described in Demain, A. L. and J. E. Davies, *Manual of Industrial Microbiology and Biotechnology*, $2^{nd}$ Ed. (1999) and Crueger, W. and A. Crueger, *Biotechnology: A Textbook of Industrial Microbiology* (1984) are applicable for preparing the cultures and carrying out the process of the present invention.

Of particular significance are compounds of the Formulae IIIA and/or IIIB:

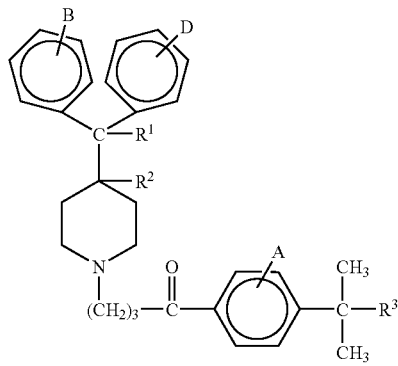

(IIIA)

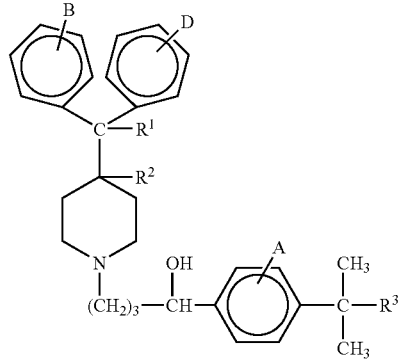

(IIIB)

wherein $R^1$, $R^2$, $R^3$, A, B, and D are defined above. Of these compounds, 4-(4-(4-hydroxydiphenyl)-1-piperidinyl)-1-hydroxybutyl)-α,α-dimethylpenylacetic acid is particularly preferred.

Another preferred class of compounds are the compounds of Formulae IVA and/or IVB:

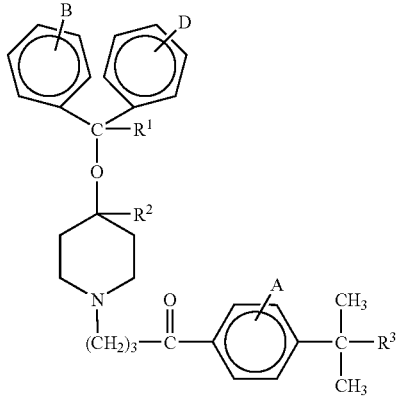
(IVA)

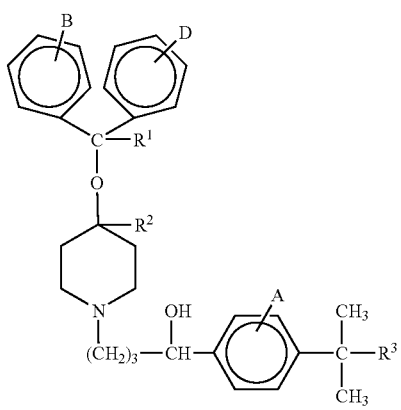
(IVB)

wherein $R^1$, $R^2$, $R^3$, A, B, and D are defined above. Of these compounds, 4-[4-[4-diphenylmethoxy)-1-piperidinyl]-oxobutyl]-α,α-dimethylphenylacetic acid is particularly preferred.

The present invention additionally relates to a process for the preparation of additional analogs of Formulae IA and/or IB starting from structures according to Formulae IIA and or IIB, with a microorganism according to the present invention.

Other illustrative examples of compounds prepared by the process of the present invention are as follows:

4-[4-[4-(hydroxydiphenylmethyl)-1-piperidinyl]-1-hydroxybutyl]-α,α-dimethylbenzeneacetic acid;
4-[4-[4-(diphenylmethyl)-1-piperidinyl]-1-hydroxybutyl]-α,α-dimethylbenzeneacetic acid;
4-[4-[4-(diphenylmethylene)-1-piperidinyl]-1-hydroxybutyl]-α,α-dimethylbenzeneacetic acid;
4-[4-[4-(hydroxydiphenylmethyl)-1-piperidinyl]-1-hydroxybutyl]-α,α-dimethyl-3-hydroxybenzeneacetic acid;
4-[4-[4-(hydroxydiphenylmethyl)-1-piperidinyl]-1-hydroxybutyl]-α,α-dimethyl-2-hydroxybenzeneacetic acid;
4-[4-[4-(diphenylmethylene)-1-piperidinyl]-1-hydroxybutyl]-α,α-dimethyl-3-hydroxybenzeneacetic acid;
4-[4-[4-(diphenylmethylene)-1-piperidinyl]-1-hydroxybutyl]-α,α-dimethylbenzeneacetic acid;
ethyl 4-[4-[4-(hydroxydiphenylmethyl)-1-piperidinyl]-1-hydroxybutyl]-α,α-dimethylbenzeneacetate;
n-pentyl 4-[4-[4-(diphenylmethyl)-1-piperidinyl]-1-hydroxybutyl]-α,α-dimethylbenzeneacetate;
ethyl 4-[4-[4-(diphenylmethylene)-1-piperidinyl]-1-hydroxybutyl]-α,α-dimethylbenzeneacetate;
methyl 4-[4-[4-(hydroxydiphenylmethyl)-1-piperidinyl]-1-hydroxybutyl]-α,α-dimethylbenzeneacetate;
ethyl 4-[4-[4-(hydroxydiphenylmethyl)-1-piperidinyl]-1-hydroxybutyl]-α,α-dimethyl-(3-hydroxybenzene)acetate;
n-propyl 4-[4-[4-(hydroxydiphenylmethyl)-1-piperidinyl]-1-hydroxybutyl]-α,α-dimethyl-(2-hydroxybenzene)acetate;
n-hexyl 4-[4-[4-(diphenylmethylene)-1-piperidinyl]-1-hydroxybutyl]-α,α-dimethyl-(3-hydroxybenzene)acetate;
ethyl 4-[4-[4-(diphenylmethylene)-1-piperidinyl]-1-hydroxybutyl]-α,α-dimethylbenzeneacetate;
4-[4-[4-(diphenylmethoxy)-1-piperidinyl]-1-hydroxybutyl]-α,α-dimethylbenzeneacetic acid;
4-[4-[4-(diphenylmethoxy)-1-piperidinyl]-1-hydroxybutyl]-α,α-dimethyl-3-hydroxybenzeneacetic acid;
4-[4-[4-(diphenylmethoxy)-1-piperidinyl]-1-hydroxybutyl]-α,α-dimethyl-2-hydroxybenzeneacetic acid;
4-[4-[4-(diphenylmethoxy)-1-piperidinyl]-1-hydroxybutyl]-α,α-dimethyl-3-hydroxybenzeneacetic acid;
4-[4-[4-(diphenylmethoxy)-1-piperidinyl]-1-hydroxybutyl]-α,α-dimethylbenzeneacetic acid;
n-pentyl 4-[4-[4-(diphenylmethoxy)-1-piperidinyl]-1-hydroxybutyl]-α,α-dimethylbenzeneacetate;
ethyl 4-[4-[4-(diphenylmethoxy)-1-piperidinyl]-1-hydroxybutyl]-α,α-dimethylbenzeneacetate;
ethyl 4-[4-[4-(diphenylmethoxy)-1-piperidinyl]-1-hydroxybutyl]-α,α-dimethyl-(3-hydroxybenzene)acetate;
n-propyl 4-[4-[4-(diphenylmethoxy)-1-piperidinyl]-1-hydroxybutyl]-α,α-dimethyl-(2-hydroxybenzene)acetate;
n-hexyl 4-[4-[4-(diphenylmethoxy)-1-piperidinyl]-1-hydroxybutyl]-α,α-dimethyl-(3-hydroxybenzene)acetate; and
ethyl 4-[4-[4-(diphenylmethoxy)-1-piperidinyl]-1-hydroxybutyl]-α,α-dimethylbenzeneacetate.

The present invention additionally relates to a process for the preparation of additional analogs of Formulae IA and/or IB starting from structures according to Formulae IIA and or IIB, with a microorganism used according to the process (or an essentially equivalent process) embodied herein.

Particularly preferred are compounds of the formulae:

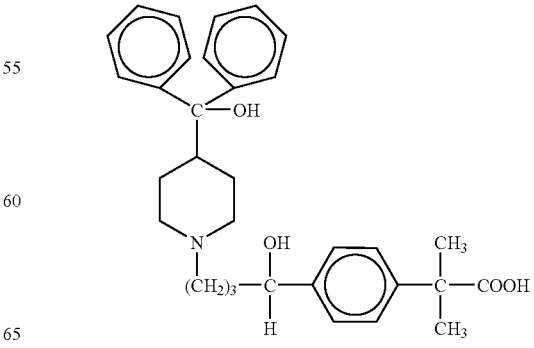

-continued

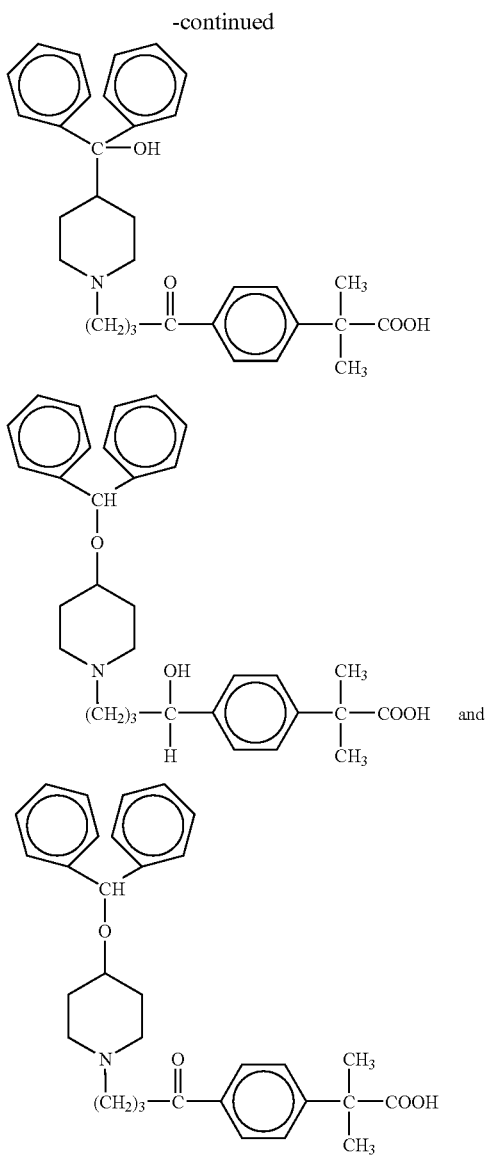

and

Optionally, both diphenyl groups from the piperidine compound may be alkyl (e.g., methyl) substituted at the position para to the methylene, such as

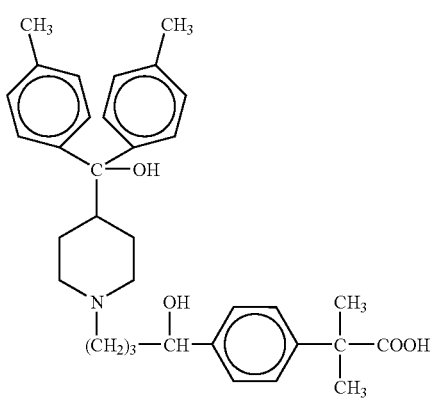

The compounds prepared by the methods of the present invention can be pharmaceutically acceptable salts in the form of inorganic or organic acid or base addition salts of the above compounds. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, anthranilic, cinnamic, salicylic, 4-aminosalicylic, 2-phenoxybenzoic, 2-acetoxybenzoic, and mandelic acid. Sulfonic acids, such as, methanesulfonic, ethanesulfonic, and β-hydroxyethanesulfonic acid are also suitable acids. Non-toxic salts of the compounds of the above-identified formulae formed with inorganic and organic bases include, for example, those alkali metals, such as, sodium, potassium, and lithium, alkaline earth metals, for example, calcium and magnesium, light metals, for example, aluminum, organic amines, such as, primary, secondary, or tertiary amines, for example, cyclohexylamine, ethylamine, pyridine, methylaminoethanol, and piperazine. These salts are prepared by conventional means, for example, by treating the piperidine derivative compounds of Formulae IA and/or IB:

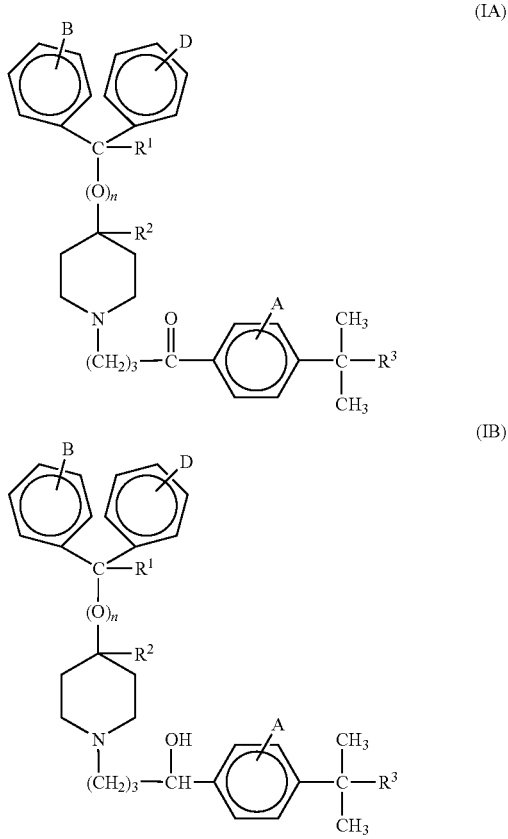

where A, B, D, n, $R^1$, $R^2$, and $R^3$ are defined above, with an appropriate acid or base.

The piperidine derivative compounds prepared by the methods of the present invention can be utilized as the biologically active components in pharmaceutical compositions. These compounds are useful as antihistamines, antiallergy agents, and bronchodilators. They may be administered alone or with suitable pharmaceutical carriers, and can be in solid or liquid form, such as, tablets, capsules, powders, solutions, suspensions, or emulsions.

The compounds prepared by the methods of this invention can be administered orally, parenterally, for example, subcutaneously, intravenously, intramuscularly, intraperitoneally, by intranasal instillation, or by application to mucous membranes, such as, that of the nose, throat, and bronchial tubes. Such application to mucous membranes can be achieved with an aerosol spray containing small particles of a compound of this invention in a spray or dry powder form.

The quantity of the compound administered will vary depending on the patient and the mode of administration and can be any effective amount. The quantity of the compound administered may vary over a wide range to provide in a unit dosage an effective amount of from about 0.01 to 20 mg/kg of body weight of the patient per day to achieve the desired effect. For example, the desired antihistamine, antiallergy, and bronchodilator effects can be obtained by consumption of a unit dosage form such as a tablet containing 1 to 50 mg of the compound of the present invention taken 1 to 4 times daily.

The solid unit dosage forms can be of the conventional type. This solid form can be a capsule, such as an ordinary gelatin type containing the compound of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The compounds prepared according to the present invention may also be administered in injectable dosages by solution or suspension of the compounds of the present invention in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the compounds in solution or suspension may be packaged in a pressurized aerosol container together with suitable propellants, for example, hydrocarbon propellants like propane, butane, or isobutane with conventional adjuvants. These compounds may be administered in a non-pressurized form, such as in a nebulizer or atomizer.

The compounds made according to the present invention can be used to treat warm blooded animals, birds, and mammals. Examples of such beings include humans, cats, dogs, horses, sheep, cows, pigs, lambs, rats, mice, and guinea pigs.

The following examples are illustrative of the invention embodied herein without being limiting in nature.

EXAMPLES

Example 1

Screening for Efficient Microbial Strains for the Transformation

Microbial cultures for reactions were inoculated using procedures described above, and specified in Table 2 below. Reaction inocula were prepared for each microorganism listed in Table 2 with 2.5 ml of each inoculum being added to 22.5 ml of medium in a 125 ml Delong flask and incubated for 24 hours at 29° C. and 225 revolutions per minute (rpm) on an orbital shaker. After this time, the pH of each culture was recorded and 0.5 ml of the cultures were transferred to individual wells of a standard format 48-well polypropylene plate (nominal volume 5 ml/well), covered with glass wool, cheesecloth, teflon-coated fabric, or other suitable gas-permeable barrier, and the reaction was initiated by the addition of 5 µl of a 25 g/L DMF stock solution of terfenadine acid metabolite (final reaction concentration of 250 mg/L). Reaction plates were incubated at 29° C. and 225 rpm inside controlled atmosphere incubation boxes and were supplied with 1 cc/min of gas containing 95% oxygen and 5% $CO_2$ gas saturated with water in a sparger humidification chamber.

Sample aliquots were collected from all cultures at reaction times between 2 and 168 hours. To 100 µl reaction samples transferred to the corresponding wells of a clean multi-well plate, 100 µl of acetonitrile were added and the plate was vortexed for one minute. 250 µl ethyl acetate was added to each well, and the plate was vortexed then sonicated for four minutes. The plate was centrifuged at 3500 rpm for 5 minutes and 200 µl of the resulting organic phase was transferred to a corresponding well of a 96-well plate. Extraction with ethyl acetate was repeated a second time on the reaction sample, and the organic phases were combined and dried under vacuum without heat. The resultant residue was redissolved in 150 μl of DMF.

Samples were analyzed by High-Pressure Liquid Chromatography (HPLC) Analysis with Atmospheric Pressure Chemical Ionization Mass Spectometry (ACPI-MS) in a 5 μm Luna C8(2) column (50 mm long×2.0 mm diameter) manufactured by Phenomenex.

TABLE 1

| Step | T. Time (min) | Dura. (min) | Flow (μL/min) | Grad. | Solvent A | Solvent B |
|---|---|---|---|---|---|---|
| 0 | −0.10 | 0.10 | 1000 | 0 | 90% | 10% |
| 1 | 0.00 | 0.50 | 1000 | 0 | 90% | 10% |
| 2 | 0.50 | 2.50 | 1000 | 1 | 40% | 60% |
| 3 | 3.00 | 2.00 | 1000 | 1 | 0% | 100% |
| 4 | 5.00 | 1.00 | 1000 | 1 | 0% | 100% |
| 5 | 6.00 | 0.50 | 1000 | 1 | 90% | 10% |

TABLE 1-continued

| Step | T. Time (min) | Dura. (min) | Flow (μL/min) | Grad. | Solvent A | Solvent B |
|---|---|---|---|---|---|---|
| 6 | 6.50 | 0.40 | 1000 | 0 | 90% | 10% |
| 7 | 6.90 | 0.10 | 1000 | 0 | 90% | 10% |

Solvent:
A = Water + 0.4% Acetic Acid,
B = Acetonitrile + 0.4% Acetic Acid.
Gradient: 0 = step gradient; 1 = linear gradient.
Detectors: UV @ 230 nm. in series with APCI-MS-MS (Triple Quadrupole Mass Spectrometer, model API 2000 by Perkin-Elmer Sciex)

Yields were calculated by integrating area counts for each chromatographic peak corresponding with a defined molecular ion by positive ionization APCI-MS. Molecular ions for terfenadine (compound 1) and terfenadine acid metabolite (compound 2) are listed in Table 2. Response factors for terfenadine acid metabolite were assumed to be identical to that for terfenadine itself.

Table 2 shows that conversions of up to 54% of terfenadine to terfenadine to acid metabolite could be obtained by some of the strains evaluated.

TABLE 2

Catalysts for oxidation of Terfenadine to Terfenadine Acid Metabolite (TAM)

| Biocatalyst I.D. | Culture Collection #[A-D] | strain type | biocatalyst preparation[E] | Culture pH | TAM production after 6 days |
|---|---|---|---|---|---|
| *Streptomyces rimosus* | NRRL-2234 | gram+ | multistage | 5 | 54% |
| *Stemphylium consortiale* | UI-4136 | fungus | multistage | 7 | 50% |
| *Gliocladium deliquescens* | NRRL-1086 | fungus | cryoready | 7 | 39% |
| *Cunninghamella bainieri* | SC-3065 | fungus | cryoready | 7 | 27% |
| *Bacillus cereus* | UI-1477 | gram+ | cryoready | 7 | 25% |
| *Cunninghamella bainieri* | SC-3065 | fungus | multistage | 7 | 18% |
| *Botrytis allii* | NRRL-2502 | fungus | multistage | 5 | 18% |
| *Cyathus striatus* | MR-356 | fungus | multistage | 5 | 11% |
| *Streptomyces rimosus* | NRRL-2234 | gram+ | cryoready | 5 | 11% |
| *Rhizopus* sp. | MR-224 | fungus | multistage | 5 | 10% |
| *Pycniodosphora dispersa* | MR-346 | fungus | multistage | 7 | 10% |
| *Absidia spinosa* var. *biappendiculata* | MR-7600 | fungus | multistage | 7 | 9% |
| *Rhizopus oryzae* | MR-RO | fungus | cryoready | 6 | 8% |
| *Cunninghamella echinulata* | NRRL-1386 | fungus | multistage | 7 | 8% |
| *Cunninghamella echinulata* | NRRL-3655 | fungus | multistage | 5 | 8% |
| *Gliocladium deliquescens* | NRRL-1086 | fungus | multistage | 7 | 7% |
| *Pseudomonas* sp. | DG-9816 | gram− | multistage | 7 | 6% |
| *Helicostylum piriforme* | QM-6945 | fungus | cryoready | 7 | 5% |
| *Aspergillus flavipes* | ATCC-1030 | fungus | multistage | 7 | 4% |
| *Mucor circinelloides f. griseo-cyanus* | IFO-4563 | fungus | multistage | 7 | 4% |
| *Gelasinospora autosteria* | MR-GA | fungus | multistage | 6 | 3% |
| *Bacillus fusiformis* | ATCC-7055 | gram+ | | 8 | 3% |
| *Streptomyces griseus* | mutant of ATCC-13273 | gram+ | multistage | 5 | 3% |
| *Rhodotorula rubra* | ATCC-36994 | yeast | cryoready | 7 | 3% |
| *Cunninghamella echinulata* | (+) | fungus | cryoready | 6 | 3% |
| *Cunninghamella echinulata* | | fungus | cryoready | 7 | 3% |
| *Mucor mucedo* | ATCC-7941 | fungus | multistage | 7 | 3% |
| *Penicillium chrysogenum* | UI-251 | fungus | cryoready | 7 | 3% |
| *Candida parasilosis* var *quercus* | ATCC-56466 | yeast | multistage | 7 | 3% |
| *Streptomyces griseus* | 10137-ATCC | gram+ | cryoready | 7 | 2% |
| *Bacillus cereus* | 14591-NRRL-B | gram+ | cryoready | 7 | 2% |
| *Streptomyces cavourensis* | 27732-ATCC | gram+ | cryoready | 7 | 2% |
| *Mucor recurvatus* | 36-MR | fungus | cryoready | 7 | 2% |
| *Penicillium notatum* | 36740-ATCC | fungus | cryoready | 7 | 2% |
| *Aspergillus carbonarium* (Bainier) Thom | 6277-ATCC | fungus | cryoready | 5 | 2% |

TABLE 2-continued

Catalysts for oxidation of Terfenadine to Terfenadine Acid Metabolite (TAM)

| Biocatalyst I.D. | Culture Collection #[A-D] | strain type | biocatalyst preparation[E] | Culture pH | TAM production after 6 days |
|---|---|---|---|---|---|
| Candida lipolytica | 8661-UI | yeast | cryoready | 4 | 2% |
| Ascoidia | MR-Asc | fungus | multistage | 7 | 2% |
| Lentinus lepidius | MR-LL | fungus | multistage | 7 | 2% |
| Pseudomonas putida (Whited) | 9866-NCIMB | bacterium | cryoready | 6 | 2% |
| Trichophyton gallinae | 1210-MR | fungus | cryoready | 7 | 1% |
| Streptomyces griseus | 13968-ATCC | gram+ | cryoready | 7 | 1% |
| Lophotrichus martinii | 177-MR | fungus | cryoready | 7 | 1% |
| Penicillium notatum | 18233-ATCC | fungus | cryoready | 7 | 1% |
| Aspergillus ochraceous | 18500-ATCC | fungus | cryoready | 6 | 1% |
| Streptomyces catenulae | 23893-ATCC | gram+ | cryoready | 7 | 1% |
| Bacillus subtilis | 2485-UI | gram+ | cryoready | 7 | 1% |
| Aspergillus alliaceus | 315-UI | fungus | cryoready | 7 | 1% |
| Mycobacterium sp. | 3683-NRRL | fungus | cryoready | 7 | 1% |
| Spicaria violacea | 3702-MR | fungus | cryoready | 7 | 1% |
| Mycobacterium bisrymcum | 463-AM | fungus | cryoready | 7 | 1% |
| Aspergillus fumigatus | 51-MR | fungus | cryoready | 7 | 1% |
| Candida lipolytica | 746-IFO | yeast | cryoready | 4 | 1% |
| Polyporus anceps | 784-F-S | fungus | cryoready | 7 | 1% |
| Candida guilliermondii | 9058-UI | yeast | cryoready | 6 | 1% |
| Cunninghamella elegans | 9245-ATCC | fungus | cryoready | 7 | 1% |
| Pseudomonas sp (naphthalene wild type) | 9816-DG | gram− | cryoready | 7 | 1% |
| Aspergillus terricola | MR-At | fungus | cryoready | 7 | 1% |
| Hansends cadaver yeast | MR-Hans | yeast | cryoready | 7 | 1% |
| Pseudomonas putida (Trevisan), toluene gene | 33015-ATCC | bacterium | cryoready | 5 | 1% |
| Fusidium coccineum | 14700-ATCC | fungus | cryoready | 7 | 1% |
| Enterococcus faecium | 51558-ATCC | bacterium | cryoready | 4 | 1% |
| Streptomyces griseus mutant | 13273-ASFZ | bacterium | cryoready | 7 | 1% |
| Streptomyces griseus mutant | 13273-#11 | bacterium | cryoready | 6 | 1% |

[A]ATCC = American Type Culture Collection, 10801 University Boulevard, Manassas, VA 20110-2209
[B]DSM = Deutsche Samlung von Mikroorganismen und Zellkulturen GmbH (German Collection of Microorganisms and Cell Cultures), Grisebachstrasse 8, D-34 Goettingen, Braunschweig, Germany.
[C]UI, SC, MR, DG, and QM = University of Iowa Culture Collection Iowa City IA, 52240
[D]NRRL = USDA Agricultural Research Service, 1815 N. University Ave. Peoria IL, 60604
[E]The designations "multistage" and "cryoready" refer to the specific method used in each example to prepare the microbial inoculum for the reaction. Complete detail for each method is described in the Detailed Description of the Invention section.

Example 2

25 ml of soybean flour medium in a 125 ml Delong flask is inoculated with a *Streptomyces rimosus* (NRRL-2234) obtained from solid slant culture, as described in Example 1. After incubating at 29° C. and 225 rpm for 24 hr, 500 µl of culture solution (pH 5.0) was transferred to a well of a 48-deepwell plate and 125 µg of terfenadine dissolved in 5 µl of DMF was added to the culture. After further cultivation in an incubation chamber at 29° C. for 7 days, the resulting microbial broth was extracted with acetonitrile and ethyl acetate. The organic phase was dried over sodium sulfate, and, then, the solvent was removed. The residue was redissolved in DMF and analyzed by HPLC-MS. Integration indicated that 76% of the recovered material was TAM.

Example 3

As described above, 2.5 ml of a frozen culture of *Gliocladium deliquescens* was cultivated in 25 ml of culture medium at pH 7 for 24 hours. 500 µl of the liquid culture was transferred to a well of a 48-deepwell plate and 125 µg of terfenadine dissolved in 5 µl of DMF was added to the culture and incubated at 29° C. for 1 week in an incubation chamber. Product recovery and analysis demonstrated that this procedure yielded 39% TAM.

Example 4

As described in Example 2, 125 µg of terfenadine dissolved in 50 ml of DMF was added to a 500 µl culture solution of *Stemphylium consortiale* (4136-UI) in a multiwell plate reactor. Product recovery and analysis demonstrated that this procedure yielded 50% TAM.

Example 5

A two-week-old solid agar culture of *Streptomyces rimosus* (ATCC 14673) was inoculated into 25 ml of soybean medium in a 125 ml Delong flask for 72 hours at 29° C. and 225 rpm. 2.5 ml of this liquid culture was transferred to 22.5 ml of soybean flour medium at pH 5 and cultivated at 29° C., 225 rpm for 24 hours. 12.5 mg of terfenadine dissolved in 250 µl of DMF was added to the culture and incubated for 1 week. Product recovery and analysis demonstrated that this procedure, carried out according to Example 2, yielded 27% TAM.

Although the invention has been described in detail for the purpose of illustration, it is understood that such details are solely for that purpose and variations can be made therein by those skilled in the art without departing from the spirit and scope of the invention which is defined by the following claims.

What is claimed:

1. A process for production of a product compound having a structure according to Formulae IA and/or IB:

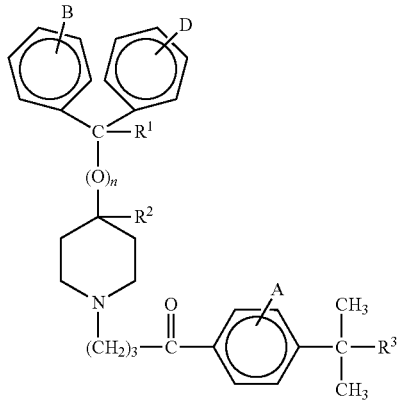
(IA)

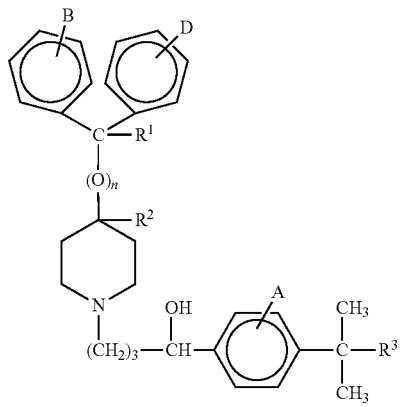
(IB)

wherein n is 0 or 1;

$R^1$ is hydrogen or hydroxy;
$R^2$ is hydrogen;
or, when n is 0, $R^1$ and $R^2$ taken together form a second bond between the carbon atoms bearing $R^1$ and $R^2$, provided that when n is 1, $R^1$ and $R^2$ are each hydrogen;

$R^3$ is —COOH or —$COOR^4$;

$R^4$ is an alkyl moiety;
A, B, and D are the substituents of their rings, each of which may be different or the same, and are selected from the group consisting of hydrogen, halogens, alkyl, hydroxy, and alkoxy, said process comprising:
incubating a starting compound having a structure according to Formulae IIA and/or IIB:

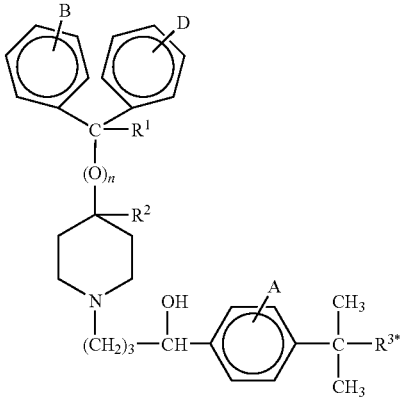
(IIA)

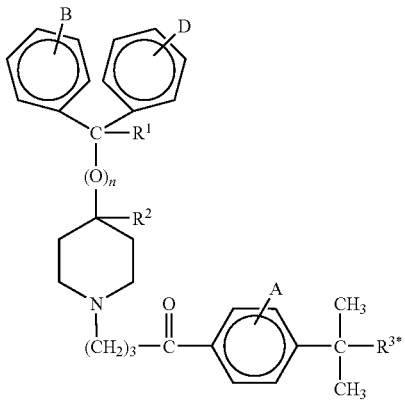

-continued (IIB)

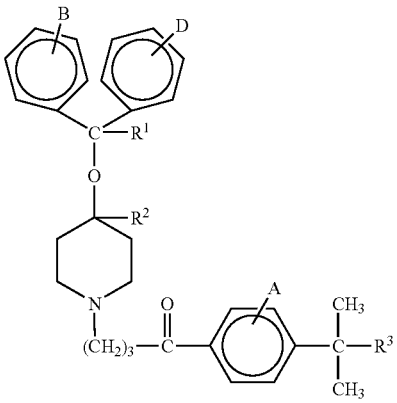

wherein $R^{3*}$ is —$CH_3$ and $R^1$, $R^2$, A, B, and D are defined above, in the presence of a microorganism under conditions effective to produce the product compound, wherein the microorganism is *Bacillus cereus, Bacillus subtilis*, or *Bacillus fusiformis*.

2. The process according to claim 1, wherein the product compound has a structure according to Formula IVA and/or IVB:

(IVA)

(IVB)

wherein $R^1$, $R^2$, $R^3$, A, B, and D are defined above.

3. The process according to claim 1, wherein prior to said incubating, the microorganism is subjected to cryopreservation or multi-stage liquid culture induction.

* * * * *